US006344461B1

(12) United States Patent
Breton et al.

(10) Patent No.: US 6,344,461 B1
(45) Date of Patent: Feb. 5, 2002

(54) TREATING SKIN WRINKLES/FINE LINES WITH CALCIUM CHANNEL INHIBITORS

(75) Inventors: Lionel Breton, Versailles; Isabelle Nonotte, Paris, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/572,234

(22) Filed: May 17, 2000

(30) Foreign Application Priority Data

May 18, 1999 (FR) .............................. 99 06290

(51) Int. Cl.[7] ...................... A61K 31/435; A61K 31/44; A61K 31/275
(52) U.S. Cl. ......................... 514/277; 514/356; 514/523
(58) Field of Search ................ 514/277, 356, 514/523

(56) References Cited

U.S. PATENT DOCUMENTS

| 5,059,606 A | | 10/1991 | Grollier et al. | |
|---|---|---|---|---|
| 5,132,119 A | * | 7/1992 | Lee et al. ................... | 424/646 |
| 5,202,130 A | * | 4/1993 | Grant et al. ................ | 424/617 |
| 5,214,041 A | | 5/1993 | Ishino et al. | |
| 5,552,162 A | * | 9/1996 | Lee ........................... | 424/646 |
| 5,554,608 A | | 9/1996 | Ahluwalia et al. | |
| 5,569,678 A | * | 10/1996 | Lee ........................... | 514/654 |
| 5,612,347 A | * | 3/1997 | Cauwenbergh et al. ..... | 514/259 |
| 5,716,625 A | * | 2/1998 | Hahn et al. ................. | 424/401 |
| 5,958,436 A | * | 9/1999 | Hahn et al. ................. | 424/401 |
| 6,060,474 A | * | 5/2000 | Williams et al. ............ | 514/253 |

FOREIGN PATENT DOCUMENTS

| BE | 1003002 A6 | 10/1991 |
|---|---|---|
| JP | 62270519 | 11/1987 |
| JP | 63022007 | 1/1988 |
| JP | 04275217 | 9/1992 |
| WO | WO 91/02497 | 3/1991 |
| WO | WO 97/18782 | 5/1997 |

* cited by examiner

Primary Examiner—William R. A. Jarvis
Assistant Examiner—Vickie Kim
(74) Attorney, Agent, or Firm—Burns, Doane, Swecker & Mathis, L.L.P.

(57) ABSTRACT

A regime or regimen for loosening/slackening and/or relaxing cutaneous and/or subcutaneous human skin tissue, advantageously for cosmetically/therapeutically treating skin wrinkles and fine lines, comprises administering to a candidate subject in need of such treatment, a thus-effective amount of at least one inhibitor of at least one calcium channel.

11 Claims, No Drawings

TREATING SKIN WRINKLES/FINE LINES WITH CALCIUM CHANNEL INHIBITORS

CROSS-REFERENCE TO PRIORITY APPLICATION

This application claims priority under 35 U.S.C. §119 of FR-99/06290, filed May 18, 1999, hereby expressly incorporated by reference.

BACKGROUND OF THE INVENTION

1. Technical Field of the Invention

The present invention relates to the administration of an effective amount of at least one inhibitor of at least one calcium channel, or composition comprised thereof, for loosening/slackening and/or relaxing cutaneous and/or subcutaneous human skin tissue, in particular for treating/reducing skin wrinkles and fine lines.

2. Description of the Prior Art

Women, and even men, currently wish to appear youthful for as long as possible and consequently seek to eradicate the signs of aging of the skin, which are reflected, in particular, by wrinkles and fine lines. In this respect, the media and the fashion world extoll products intended to maintain for as long as possible skin which is radiant and wrinkle-free, which are signs of youthful skin, and all the more so since physical appearance favorably influences the psyche and/or the morale.

Heretofore, wrinkles and fine lines were treated using cosmetic products containing active agents acting on the skin, for example by moisturizing same or improving its cell renewal or, alternatively, by promoting the synthesis of collagen, of which skin tissue is composed. However, to date it is not known to reduce/treat wrinkles by intervening on the contractile elements present in the skin.

Thus, it is known that the dermal muscles of the face are under the control of motor nerve afferences of the facial nerve and that, moreover, the interlobular septa of the hypoderm contain within them fibers which constitute a striated muscle tissue (panniculus carnosus). Moreover, it too is known that a sub-population of dermal fibroblasts, known as myofibroblasts, has contractile characteristics in common with muscle tissue.

Calcium is the final messenger of muscle contraction. The contraction-relaxation cycle is due to variations in the concentration of cytoplasmic calcium of from $10^{-8}$ to $10^{-5}$ M in the contractile cell.

In muscle at rest, the intracellular concentration of free calcium remains less than $10^{-8}$ M although the extracellular concentration is 10,000 times higher and although the force represented by the electrochemical potential gradient has a tendency to effect calcium penetration into the cell. This resting or quiescent state is due to the low permeability to calcium of the cell membrane and to the activity of various mechanisms which sequester calcium or expel it from the cell. Various cytoplasmic proteins, in particular parvalbumins, thus have the capacity to bind calcium. Among the intracellular organelles, the endoplasmic reticulum can accumulate and release calcium under conditions that are compatible with physiological regulations.

An increase in the level of calcium in the cytoplasm of the myocyte allows the activation of the contractile machinery. The influx of calcium into the intracellular compartment (depolarization) participates in decreasing the potential difference between the outside and the inside and thus renders the cell more excitable.

Specifically, the depolarization of the transverse tubules (invagination of the cell membrane) which propagates to the longitudinal tubules (sarcoplasmic reticulum) induces the momentary release of intracellular calcium by these tubules. In the presence of calcium, the contractile proteins of striated muscle have an ATPase activity which provides the energy required for the contraction.

Conversely, the relaxation of striated muscle takes place when a new ATP molecule binds to the contractile proteins. The intracellular calcium then returns to the intracellular compartment and its concentration once again becomes close to a value of $10^{-8}$ M.

Moreover, it too has been shown that botulinum toxin, used originally to treat spasms, can act on states of muscular spasticity (see A. Blitzer et al., *Arch. Otolaryngol. Head Neck Surg.*, 119, pages 1018 to 1022 (1993)), and on wrinkles of the glabella which are the wrinkles between the eyebrows (see J. D. Carruthers et al., *J. Dermatol. Surq. Oncol.*, 18, pages 17 to 21 (1992)). Consequently, it is possible to affect the nerve component of wrinkles.

In the peripheral nervous system, the junction between a nerve and a muscle constitutes the neuro-muscular plaque, upstream of which is the efferent nerve pathway known as the motorneuron. Moreover, the cell membranes of each nerve fiber also comprise numerous ion channels, and in particular calcium ion channels, which are capable of allowing the corresponding element, which in this particular case is calcium, to traverse in ionic state.

The important role of calcium and of regulating its intracellular concentration in the phenomena of muscle contraction/relaxation can thus be readily appreciated.

Regulation of the intracellular concentration of calcium is only possible because the efflux of calcium corrects the influx. This can only be ensured by an expulsion of the cellular calcium via one or more mechanisms capable of overcoming the electrochemical potential gradient mentioned above.

Two types of mechanism can intervene: a calcium pump, which actively expels the cations at the expense of the hydrolysis of ATP, and a movement of calcium coupled to a movement of sodium. In most cells, the ATP-dependent calcium pump operates more efficiently in the presence of calmodulin which increases its affinity.

In order best to describe the changes in permeability to calcium, it is currently common to consider that this permeability corresponds to the opening of membrane calcium channels, these channels being operated by variations in the membrane potential (VOC) or activation of membrane receptors (ROC). To date, six VOC types of calcium channels (L, N, T, P, Q and R) have been identified.

It is thus understood from the account hereinabove that the contraction or hypercontraction of certain facial muscles results in the appearance of wrinkles. This muscle activation is itself induced by a variation in the flow of calcium through transmembrane calcium channels.

SUMMARY OF THE INVENTION

It has now unexpectedly and surprisingly been determined, after numerous clinical tests, that contractile muscle fiber, which is under the direct control of the neural motor influx, plays an essential role in the formation of wrinkles, and that modulating the neural motor influx and controlling the contraction of muscle fibers serve an essential function in the formation of wrinkles. Thus, modulating the motor contraction attenuates not only wrinkles, but also fine lines and also has a "smoothing" effect on the skin's microrelief. It too has been found that cutaneous and subcutaneous tissues comprise calcium channels, which has not been envisaged hitherto.

No link had hitherto been established between the calcium channels of subcutaneous muscle and/or nerve tissue and wrinkles, and to date it had not been considered to treat wrinkles by acting on the calcium channels.

Thus, the present invention features influencing calcium channels in order to decontract (loosen/slacken) or relax skin tissues, and thus reduce wrinkles and fine lines.

As early as 1965, studies were carried out by T. Godfraind to investigate the mechanisms by which certain medicinal substrates inhibit the contractile response to several vasoactive agents. The hypothesis proposed was that the permeability of the membrane to calcium might be inhibited by pharmacological agents, which would constitute the common mechanism on which multivalent antagonists would act.

The simplest experimental technique for demonstrating that a pharmacological agent is capable of inhibiting the influx of calcium entails preincubating a smooth muscle in a calcium-free physiological solution, depolarizing it in a KCl-rich solution and gradually increasing the calcium concentration in the infusion solution. This brings about an increase in the tension of the muscle, whose value changes up to a maximum as a function of the calcium concentration. When this protocol is repeated in the presence of a substrate supposed to inhibit the influx of calcium, as was carried out for the first time with cinnarizine, the contractile responses are inhibited in a dose-dependent manner. A similar concept was applied to describe the action of verapamil on the heart. Verapamil was originally considered as a β-blocker, but its action is more complex since it exerts an inhibitory action on the excitation-contraction coupling. On the papillary muscle, verapamil eliminates the contraction by very faintly modifying the action potential. It is this observation which resulted in verapamil being considered as a calcium antagonist.

Thus, the present invention features the administration of an effective amount of at least one inhibitor of at least one calcium channel, or composition comprised thereof, to relax and/or decontract (loosen/slacken) cutaneous and/or subcutaneous tissue.

This invention also features administration of an effective amount of at least one inhibitor of at least one calcium channel, or composition comprised thereof, to smooth out the skin.

Too, the present invention features administration of an effective amount of at least one inhibitor of at least one calcium channel, or composition comprised thereof, to attenuate and/or eliminate the skin's microrelief.

In particular, this invention features administration of an effective amount of at least one inhibitor of at least one calcium channel, or composition comprised thereof, to combat, curatively and/or preventively, skin wrinkles and fine lines.

The present invention is particularly effective for reducing wrinkles and fine lines.

Specifically, the relaxation and/or decontraction of cutaneous and/or subcutaneous tissue corresponds to a muscular decontraction or relaxation.

DETAILED DESCRIPTION OF BEST MODE AND SPECIFIC/PREFERRED EMBODIMENTS OF THE INVENTION

More particularly according to the present invention, for a substance to be recognized as a calcium-channel inhibitor, also referred to herein as a calcium inhibitor, it must have the capacity to reduce the intracellular calcium concentration or reduce the binding of calcium to the intracellular proteins such as, for example, calmodulin, as described, in particular, by Galizzi, J. P. et al., *J. Biol. Chem.*, 262 p.6947 (1987) or Y. Okamiya et al., *Eur. J. Pharmacol.*, 205, p.49 (1991) or J. A. Wagner et al., *J. Neurosci.*, 8, p. 3354 (1988) or H. R. Lee et al., *Life Sci.*, 35, p. 721 (1984) or Schoemaker H. and Lauger S., *Eur. J. Pharmacol.*, 111 p. 273 (1985) or I. J. Reynolds et al., *J. Pharmacol. Exp. Ther.*, 237 p. 731 (1986).

For the purposes of the present invention, a substance or substrate is recognized as being a relaxant when it elicits a relaxation effect on contracted muscle tissue and/or exhibits an inhibitory effect in an experimental model of nerve-muscle juncture (motor plate), in particular in the model described by W. Steinbrecher in: "Electrodes for stimulation and bioelectric potential recording", *Ed. Biomerstechnich*, pages 96–98 (1988).

The effective amount of inhibitor of at least one calcium channel which is useful according to the invention obviously depends on the desired effect and can thus vary over a wide range.

In order to provide an order of magnitude, it is possible according to the invention to administer an inhibitor of at least one calcium channel in an amount advantageously ranging from 0.0001% to 10% of the total weight of the composition and preferably in an amount ranging from 0.001% to 5% of the total weight of the composition.

Exemplary calcium-channel inhibitors according to the invention include those agents that are active on the plasma membrane, calcium-complexing agents and/or calcium-influx inhibitors, for instance phenylalkylamines such as, for example, verapamil, anipamil, gallopamil, devapamil, falipamil and tiapamil, dihydropyridines such as, for example, nifedipine, amlodipine, dazodipine, felodipine, isradipine, lanicardipine, nimodipine, nisoldipine, nitrendipine and ryosidine, benzothiazepines such as, for example, Diltiazem, and diphenylpiperazines such as, for example, cinnarizine and flunarizine; or agents that are active inside the cell, which have an effect on the release of the intracellular calcium reserves or on inhibition of the formation of the calcium/calmodulin complex. These are, for example, agents which have an effect on the sarcoplasmic reticulum, such as, for example, dantrolene and TMB-8, calmodulin antagonists such as, for example, phenothiazine, trifluoperazine and chlorpromazine or naphthalene derivatives, or local anaesthetics such as dibucaine, or dopamine antagonists such as pimozide, haloperidol or calmidazolium.

Preferably, agents that are active on the plasma membrane, calcium-influx inhibitors or calcium-complexing agents are administered. Very preferably, calcium-influx inhibitors such as verapamil are administered.

The compositions according to the invention can be provided in any pharmaceutical form normally employed for topical, injectable or oral administration.

The compositions according to the invention can be applied either locally, i.e. topically, or by subcutaneous and/or intradermal injection.

Preferably, the subject compositions are topically applied.

The amounts of the various constituents in the compositions according to the invention are those used conventionally in the technical fields under consideration and are appropriate for their pharmaceutical form.

For topical application, the compositions of the invention comprise a medium (vehicle, diluent or carrier) which is compatible with human skin. These compositions can be, in particular, in the form of aqueous, alcoholic or aqueous/alcoholic solutions, ointments, lotions, gels, water-in-oil or oil-in-water emulsions having the appearance of a cream or a gel, microemulsions or aerosols, or alternatively in the form of vesicular dispersions containing ionic and/or non-ionic lipids. These pharmaceutical dosage units are formulated according to the usual techniques in the fields under consideration.

These compositions for topical application can constitute, in particular, a protective care composition for the face, for the neck, for the hands or for the body (for example day creams, night creams, antisun creams or oils and body milks), a makeup composition (for example a foundation) or an artificial tanning composition.

When the composition of the invention is an emulsion, the proportion of fatty substances it contains advantageously ranges from 5% to 80% by weight, and preferably from 5% to 50% by weight, relative to the total weight of the composition. The fatty substances and the emulsifiers used in the composition in emulsion form are selected from among those used conventionally in the cosmetic or pharmaceutical field.

Exemplary fatty substances include mineral oils (petroleum jelly), plant oils (liquid fraction of karite butter) and hydrogenated derivatives thereof, animal oils, synthetic oils (perhydrosqualene), silicone oils (polydimethylsiloxane) and fluoro oils. Other fatty substances which are exemplary are fatty alcohols (cetyl alcohol or stearyl alcohol), fatty acids (stearic acid) and waxes.

The emulsifiers are advantageously present in the subject compositions in a proportion ranging from 0.3% to 30% by weight, and preferably from 0.5 to 30% by weight, relative to the total weight of the composition.

In known fashion, the compositions of the invention can also contain adjuvants and additives that are common in the corresponding fields, such as hydrophilic or lipophilic gelling agents, preservatives, antioxidants, solvents, fragrances, fillers, UV-screening agents and dyestuffs and colorants. Moreover, these compositions can contain hydrophilic or lipophilic active agents. The amounts of these various adjuvants, additives or active agents are those used conventionally in the cosmetic or pharmaceutical field, and, for example, constitute from 0.01% to 20% of the total weight of the composition. Depending on their nature, these adjuvants or active agents can be introduced into the fatty phase, into the aqueous phase and/or into lipid vesicles.

Exemplary such active agents which can be included in the compositions of the invention, particularly representative are those active agents having an effect on the treatment of wrinkles or fine lines, and in particular keratolytic active agents. By the term "keratolytic" is intended an active agent exhibiting desquamating, exfoliant or scrubbing properties, or an active agent capable of softening the horny layer of the skin.

Exemplary active agents having an effect on the treatment of wrinkles or fine lines include, in particular, hydroxy acids and retinoids.

Exemplary such hydroxy acids include α-hydroxy acids or β-hydroxy acids, which can be linear, branched or cyclic, and saturated or unsaturated. The hydrogen atoms in the carbon-based backbone chain can, in addition, be substituted with halogens, halogen-containing, alkyl, acyl, acyloxy, alkoxycarbonyl or alkoxy radicals having from 2 to 18 carbon atoms.

Exemplary hydroxy acids include, in particular, glycolic acid, lactic acid, malic acid, tartaric acid, citric acid, 2-hydroxyalkanoic acid, mandelic acid, salicylic acid and alkyl derivatives thereof such as 5-n-octanoylsalicylic acid, 5-n-dodecanoylsalicylic acid, 5-n-decanoylsalicylic acid, 5-n-octylsalicylic acid, 5-n-heptyloxysalicylic acid or 4-n-heptyloxysalicylic acid, and 2-hydroxy-3-methylbenzoic acid or alkoxy derivatives thereof, such as 2-hydroxy-3-methoxybenzoic acid.

And exemplary retinoids include, in particular, retinoic acid (all-trans or 13-cis) and derivatives thereof, retinol (vitamin A) and esters thereof such as retinol palmitate, retinol acetate and retinol propionate, as well as salts thereof.

These active agents are advantageously formulated, in particular, in concentrations ranging from 0.0001% to 5% by weight relative to the total weight of the composition.

The compositions of the invention are advantageously formulated as cosmetic or dermatological compositions.

Preferably, the compositions of the present invention are formulated as cosmetic compositions.

This invention also features a regime/regimen for the cosmetic treatment of wrinkles and/or fine lines, comprisingly topically applying onto the skin a cosmetic composition which comprises, in a cosmetically acceptable medium, an effective amount of at least one inhibitor of at least one calcium channel.

By the expression "cosmetically acceptable medium" is intended a vehicle, diluent or carrier which is compatible with the skin, the scalp and/or mucous membranes.

The cosmetic treatment of the invention can be carried out, in particular, by topically applying the cosmetic composition as described above, according to the usual technique for administering these compositions. For example: application of creams, gels, sera, lotions, ointments, makeup-removing milks or antisun compositions to the skin, or spray compositions.

In order to further illustrate the present invention and the advantages thereof, the following specific examples are given, it being understood that same are intended only as illustrative and in nowise limitative.

In said examples to follow, all parts, and percentages are given be weight, except where otherwise indicated.

EXAMPLE 1

Measurement of the Activity of a Calcium-channel Inhibitor in a Model of Nerve/muscle Juncture (neuromuscular juncture) Obtained in an Isolated Phrenic Nerve/diaphragm Preparation: Investigation of a Muscle-relaxant Effect:

The phrenic nerve and the diaphragm were carefully isolated and placed in a 50 ml cuvette filled with survival liquid (Krebs Henseleit liquid) maintained at a temperature of 37° C. and oxygenated with a mixture of 95% oxygen and 5% $CO_2$.

The variations in the tension of the diaphragm were then recorded with an initial preload of several grams.

After a 30 minute period of relaxation, the diaphragm was stimulated indirectly via the phrenic nerve.

On each preparation, the effect of the test products was evaluated, in a first stage, on the contractions induced by indirect stimulation via stimulation on the phrenic nerve (0.1 to 7 volts, 0.3 ms, 0.1 Hz) at increasing and cumulative concentrations from $10^{-9}$ M to $10^{-4}$ M.

In the event of an effect at the end of the test, the influence of the test products was evaluated on the contractions induced by direct stimulation on the muscle (5 to 50 volts, 0.3 ms, 0.2 Hz) at a concentration of $10^{-4}$ M only, in order to determine the mechanism of action of the test product.

The following results were obtained in the motor plate model with Verapamil.

| Verapamil concentration | % inhibition (indirect stimulation) | % inhibition (direct stimulation) |
|---|---|---|
| $10^{-4}$ M | 100 | 22 |

EXAMPLE 2

In this example, specific compositions according to the invention were formulated:

Composition 1: Facial Care Lotion:

| | |
|---|---|
| Verapamil | 0.05% |
| Antioxidant | 0.05% |
| Preservative | 0.03% |
| Ethanol (solvent) | 8.00% |
| Water | qs 100% |

The lotion obtained treats wrinkles when used repeatedly (application twice a day for one month).

Composition 2: Facial Care Gel:

| | |
|---|---|
| Verapamil | 0.10% |
| Hydroxypropylcellulose* | 1.00% |
| Preservative | 0.30% |
| Ethanol (solvent) | 15.00% |
| Antioxidant | 0.05% |
| Water | qs 100% |

*Klucel H marketed by Hercules (gelling agent).

The gel obtained is useful for treating wrinkles. It can be applied daily morning and evening for one month.

Composition 3: Facial Care Cream (oil-in-water emulsion):

| | |
|---|---|
| Nimodipine | 1.00% |
| Glyceryl stearate (emulsifier) | 2.00% |
| Polysorbate 60 (Tween 60 marketed by ICI) (emulsifier) | 1.00% |
| Stearic acid | 1.40% |
| Triethanolamine (neutralizing agent) | 0.70% |
| Carbomer (Carbopol 940 marketed by Goodrich) | 0.40% |
| Liquid fraction of karite butter | 12.00% |
| Perhydrosqualene | 12.00% |
| Preservative | 0.30% |
| Fragrance | 0.50% |
| Antioxidant | 0.05% |
| Water | qs 100% |

An unctuous white cream is obtained, which is useful for treating wrinkles and fine lines, and which can be applied daily.

Composition 4: Facial Care Cream (oil-in-water emulsion):

| | |
|---|---|
| Verapamil | 0.10% |
| Glyceryl mono-, distearate | 2.00% |
| Cetyl alcohol | 1.50% |
| Cetylstearyl alcohol/33 EO oxyethylenated cetylstearyl alcohol mixture | 7.00% |
| Polydimethylsiloxane | 1.50% |
| Liquid petroleum jelly | 17.50% |
| Preservative | 0.30% |
| Fragrance | 0.50% |
| Glycerol | 12.50% |
| Water | qs 100% |

While the invention has been described in terms of various preferred embodiment, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. The regime or regimen for treating skin wrinkles and fine lines, comprising administering to a candidate subject in need of such treatment, a thus-effective amount of at least one calcium channel inhibitor.

2. The regime or regimen as defined by claim 1, for reducing skin wrinkles and fine lines.

3. The regime or regimen as defined by claim 1, for attenuating the microrelief of the skin.

4. The regime or regimen as defined by claim 1, comprising topically applying said effective amount of at least one calcium channel inhibitor onto the skin of said candidate subject in need of such treatment.

5. The regime or regimen as defined by claim 1, said at least one calcium channel inhibitor comprising an agent active on the plasma membrane, a calcium-influx inhibitor, a calcium-complexing agent, or an agent active inside the cell, which have an effect on the release of intracellular calcium reserves or an inhibition of the formation of the calcium/calmodulin complex.

6. The regime or regimen as defined by claim 5, said at least one calcium channel inhibitor comprising a phenylalkylamine, a dihydropyridine, a benzothiazepine, or a diphenylpiperazine.

7. The regime or regimen as defined by claim 6, said at least one calcium channel inhibitor comprising verapamil, anipamil, gallopamil, devapamil, falipamil, tiapamil, nifedipine, amlodipine, dazodipine, felodipine, isradipine, lanicardipine, nimodipine, nisoldipine, nitrendipine, ryosidine, Diltiazem, cinnarizine, or flunarizine.

8. The regime or regimen as defined by claim 7, said at least one calcium channel inhibitor comprising verapamil.

9. The regime or regimen as defined by claim 5, said at least one calcium channel inhibitor comprising an agent active on the sarcoplasmic reticulum, a calmodulin antagonist, a naphthalene compound, or a dopamine antagonist.

10. The regime or regimen as defined by claim 9, said at least one calcium channel inhibitor comprising dantrolene, TMB-8, phenothiazine, trifluoperazine, chlorpromazine, dibucaine, pimozide, haloperidol, or calmidazolium.

11. The regime or regimen as defined by claim 1, comprising subcutaneously and/or intradermally injecting said at least one calcium channel.

* * * * *